United States Patent
Drillon et al.

(10) Patent No.: US 9,358,184 B2
(45) Date of Patent: Jun. 7, 2016

(54) COMPOSITION COMPRISING A NONIONIC SURFACTANT, A POLYCONDENSATE OF ETHYLENE OXIDE AND OF PROPYLENE OXIDE AND A MONOALCOHOL

(75) Inventors: Damien Drillon, Paris (FR); Stephanie Neplaz, Paris (FR); Beatrice Thoms, Deuil la Barre (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/111,194

(22) PCT Filed: Apr. 13, 2012

(86) PCT No.: PCT/EP2012/056762
§ 371 (c)(1),
(2), (4) Date: Jan. 24, 2014

(87) PCT Pub. No.: WO2012/140192
PCT Pub. Date: Oct. 18, 2012

(65) Prior Publication Data
US 2014/0128305 A1    May 8, 2014

Related U.S. Application Data

(60) Provisional application No. 61/478,580, filed on Apr. 25, 2011.

(30) Foreign Application Priority Data

Apr. 15, 2011    (FR) ..................... 11 53314

(51) Int. Cl.
| | | |
|---|---|---|
| *A61K 8/34* | (2006.01) |
| *A61K 8/60* | (2006.01) |
| *A61K 8/86* | (2006.01) |
| *A61Q 5/02* | (2006.01) |
| *C11D 1/72* | (2006.01) |
| *C11D 1/722* | (2006.01) |
| *C11D 1/825* | (2006.01) |
| *C11D 3/22* | (2006.01) |
| *A61K 8/02* | (2006.01) |
| *A61Q 5/12* | (2006.01) |
| *A61K 8/39* | (2006.01) |

(52) U.S. Cl.
CPC .................. *A61K 8/0204* (2013.01); *A61K 8/34* (2013.01); *A61K 8/39* (2013.01); *A61K 8/604* (2013.01); *A61K 8/86* (2013.01); *A61Q 5/02* (2013.01); *A61Q 5/12* (2013.01)

(58) Field of Classification Search
CPC ............. A61K 8/34; A61K 8/60; A61K 8/86; A61Q 5/02; C11D 1/72; C11D 1/722; C11D 1/825; C11D 3/2006; C11D 3/22; C11D 3/3707
USPC ................. 510/119, 155, 421, 474, 475, 505; 424/488, 70.13, 70.31
See application file for complete search history.

(56) References Cited

FOREIGN PATENT DOCUMENTS

| EP | 1709996 A1 | 10/2006 |
|---|---|---|
| WO | 9804660 A1 | 2/1998 |
| WO | WO 2012/076537 * 6/2012 ............... A61K 8/34 |

OTHER PUBLICATIONS

International Search Report for PCT/EP2012/056762.
Porter, M.R., "Handbook of Surfactants," published by Blackie & Son, 1991, pp. 116-178.
Schmolka, I.R., "A Review of Block Polymer Surfactants," Journal of the American Oil Chemists' Society, vol. 54, No. 3, XP009037148, Jan. 1, 1997, pp. 110-116.
English language abstract of EP 1 709 996.

* cited by examiner

*Primary Examiner* — Brian P Mruk
(74) *Attorney, Agent, or Firm* — The Marbury Law Group, PLLC

(57)    ABSTRACT

The present invention relates to a composition comprising: (i) at least 20% by weight, relative to the total weight of the composition, of at least one C2-C4 monoalcohol; (ii) at least one polycondensate of ethylene oxide and of propylene oxide; and (iii) at least one nonionic surfactant other than the polycondensates (ii). The invention also relates to the use of this composition for cleansing the hair, and to a process for cleansing the hair using this composition.

16 Claims, No Drawings

COMPOSITION COMPRISING A NONIONIC SURFACTANT, A POLYCONDENSATE OF ETHYLENE OXIDE AND OF PROPYLENE OXIDE AND A MONOALCOHOL

This is a national stage application of PCT/EP2012/056762, filed internationally on Apr. 13, 2012, which claims priority to U.S. Provisional Application No. 61/478,580, filed on Apr. 25, 2011, as well as French Application No. 1153314, filed on Apr. 15, 2011, all of which are incorporated herein by reference in their entireties.

The present invention relates to a composition, especially a hair composition, for cleansing keratin materials, in particular the hair, comprising, in a cosmetically acceptable aqueous medium, at least one C2-C4 monoalcohol, at least one nonionic surfactant and at least one polycondensate of ethylene oxide and of propylene oxide; the invention also relates to a hair cleansing process using this composition.

Hair has a tendency to lose some of its qualities under the action of factors such as natural greasiness, sweat, the appearance of squamae, pollution and humidity. These factors harm the visual appearance and the feel of the hair. Thus, the greasiness and, possibly, pollution make the hair lank, the hair then having a tendency to associate in packets. The hair is then difficult to style, has an unpleasant greasy sheen and a waxy feel that is also unpleasant. The magnitude of the consequences of these factors, which are almost all inevitable, is very variable. It depends, for example, on the quality of the hair, its length and its adopted style.

Be that as it may, shampoos are used to combat these drawbacks. Specifically, washing with detergent compositions is very effective; it removes the soiling and dandruff. It is then possible, on drying, to place the head of hair in the desired shape. However, the beneficial effect of shampooing fades out and, within a few days, the problems described above once again arise. Consequently, there is a tendency to increase the frequency of shampooing. Moreover, to perform shampooing, a source of water, preferably hot or warm water, is needed.

In addition, shampoo compositions are based on large amounts of surfactants that may cause discomfort such as stinging on the scalp or in the eyes.

To cleanse the hair more rapidly and to avoid wetting the hair, it has already been proposed to use "dry" shampoos. This technique consists in applying absorbent particles to the hair and then in actively brushing the head of hair to remove the particles therefrom. However, in general, total removal of the particles is very difficult to obtain. The results are not very satisfactory: the hair has poor sheen and a coarse, crunchy feel. Furthermore, the pulverulent nature of the product does not make it comfortable to apply, or optimal as regards the harmlessness.

The aim of the present invention is especially to solve the above problems. More specifically, the present invention is directed towards proposing a process for cleansing the hair that leads, at the end of the operation, to hair that has a neutral feel and visual appearance.

After extensive research conducted in this matter, it has been found by the Applicant, entirely surprisingly and unexpectedly, that this aim and others can be achieved by using compositions, especially cosmetic compositions, and in particular hair compositions, which are preferably intended for cleansing the hair, comprising:

(i) at least 20% by weight, relative to the total weight of the composition, of at least one C2-C4 monoalcohol,
(ii) at least one polycondensate of ethylene oxide and of propylene oxide, and
(iii) at least one nonionic surfactant other than the polycondensates (ii).

In comparison with conventional dry shampoos, the composition according to the invention avoids the presence of residues, and avoids giving the hair a crunchy feel. The cosmetic properties are improved.

Hair cleansed with the compositions according to the invention has the characteristics of clean hair: the hair has a natural feel, is shiny (the greasy appearance has disappeared), the head of hair is light and airy, and there is no dandruff. Furthermore, the hair is more managed, more supple and smoother. In addition, the treatment removes the unpleasant odours. Finally, its innovative presentation form in the form of a jelly overcomes the pulverulent aspect and facilitates the application.

A subject of the invention is also the cosmetic use of a composition as defined above for cleansing the hair and/or the scalp.

A subject of the present invention is also a process for cleansing the hair and/or the scalp, the said process being characterized in that a composition as defined above is applied to the hair, preferably dry hair, and the hair is then optionally dried.

In the description, the term "at least one" is equivalent to "one or more".

The C2-C4 monoalcohols are linear or branched. They are especially chosen from ethanol, isopropanol, tert-butanol and n-butanol, and mixtures thereof.

The C2-C4 monoalcohols are preferably present in a concentration ranging from 20% to 70% by weight, preferably from 20% to 60% by weight and better still from 25% to 45% by weight, relative to the total weight of the composition.

Examples of nonionic surfactants other than the polycondensates of ethylene oxide and of propylene oxide in the composition used according to the invention, are described in the *Handbook of Surfactants* by M. R. Porter, published by Blackie & Son (Glasgow and London), 1991, pp. 116-178. They are chosen in particular from polyethoxylated, polypropoxylated or polyglycerolated fatty alcohols, polyethoxylated, polypropoxylated or polyglycerolated fatty alpha-diols, polyethoxylated, polypropoxylated or polyglycerolated (C1-C20)alkylphenols, and polyethoxylated, polypropoxylated and/or polyglycerolated fatty acids, these compounds bearing a fatty chain comprising, for example, from 8 to 30 carbon atoms, it being possible for the number of ethylene oxide or propylene oxide groups to range in particular from 2 to 50 and for the number of glycerol groups to range in particular from 2 to 30.

Mention may also be made of optionally oxyethylenated fatty acid esters of sorbitan, fatty acid esters of sucrose, polyoxyalkylenated fatty acid esters, optionally oxyalkylenated alkylpolyglycosides, alkylglucoside esters, derivatives of N-alkylglucamine and of N-acylmethylglucamine, aldobionamides and amine oxides.

The nonionic surfactants are preferably chosen from polyethoxylated, polypropoxylated or polyglycerolated fatty alcohols, bearing a fatty chain comprising, for example, from 8 to 30 carbon atoms, the number of ethylene oxide and/or propylene oxide groups possibly ranging especially from 2 to 50, and the number of glycerol groups possibly ranging especially from 2 to 30, and optionally oxyalkylenated alkylpolyglycosides, and mixtures thereof.

Nonionic surfactants that will even more preferentially be used include alkylpolyglycosides and especially alkylpolyglucosides (APG) bearing an alkyl group comprising from 8 to 30 carbon atoms (C8-C30-alkyl polyglucosides) and preferably 8 to 16 carbon atoms, for instance decyl glucoside (Alkyl-C9/C11-polyglucoside (1.4)), such as the product sold under the name Mydol 10 by the company Kao Chemicals, the product sold under the name Plantaren 2000 UP or Plantacare 2000 UP by the company Henkel, and the product sold under the name Oramix NS 10 by the company SEPPIC; caprylyl/capryl glucoside such as the product sold under the name Oramix CG 110 by the company SEPPIC; lauryl glucoside, such as the products sold under the names Plantaren 1200 N and Plantacare 1200 by the company Henkel; and cocoyl glucoside, such as the product sold under the name Plantacare 818/UP by the company Henkel.

The composition may also comprise a mixture of these nonionic surfactants.

The concentrations of the various surfactants are preferably chosen such that the composition does not foam when applied to the hair. Preferably, the nonionic surfactants are present in a concentration ranging from 0.01% to 5% by weight, better still from 0.01% to 2%, more particularly from 0.05% to 1% by weight, even more particularly from 0.075% to 0.5% by weight and even better still from 0.1% to 0.25% by weight, relative to the total weight of the composition.

The composition according to the invention comprises at least one polycondensate of ethylene oxide and of propylene oxide. This polycondensate is preferably a polyethylene glycol/polypropylene glycol/polyethylene glycol triblock polycondensate.

The polycondensate(s) of ethylene oxide and of propylene oxide may in particular have the formula (I) below:

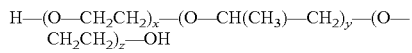

$$H—(O—CH_2CH_2)_x—(O—CH(CH_3)—CH_2)_y—(O—CH_2CH_2)_z—OH$$

in which x and z range from 2 to 150 and y ranges from 1 to 100.

In formula (I) above, preferably x and z range from 5 to 100 and y ranges from 10 to 80, better still x and z range from 8 to 50 and y ranges from 20 to 60 and even better still x and z range from 10 to 20 and y ranges from 25 to 40. According to one particular embodiment, x and z are identical.

The polycondensate of ethylene oxide and of propylene oxide that is useful in the composition of the invention preferably has a weight-average molecular weight ranging from 250 to 19 000, better still ranging from 1200 to 15 000, in particular ranging from 1500 to 10 000 and even better still ranging from 1500 to 5000. Advantageously, the said polycondensate of ethylene oxide and propylene oxide has a cloud point, at 10 g/l in distilled water, of greater than or equal to 20° C. and preferably of greater than or equal to 60° C. The cloud point is measured according to standard ISO 1065.

As polycondensates of ethylene oxide and of propylene oxide that may be used according to the invention, mention may be made of the polyethylene glycol/polypropylene glycol/polyethylene glycol triblock polycondensates sold under the name Synperonic, for instance Synperonic® PE/F32 (INCI name: Poloxamer 108), Synperonic® PE/F108 (INCI name: Poloxamer 338), Synperonic® PE/L44 (INCI name: Poloxamer 124), Synperonic® PE/L42 (INCI name: Poloxamer 122), Synperonic® PE/F127 (INCI name: Poloxamer 407), Synperonic® PE/F88 (INCI name: Poloxamer 238), Synperonic® PE/L64 (INCI name: Poloxamer 184), Synperonic® PE/F88 (INCI name: Poloxamer 238), Synperonic® PE/F87 (INCI name: Poloxamer 237) from the company Croda, or Lutrol® F68 (INCI name: Poloxamer 188) from the company BASF.

The polycondensates of ethylene oxide and of propylene oxide are preferably present in a concentration ranging from 0.1% to 10% by weight and more particularly from 0.5% to 5% by weight relative to the total weight of the composition.

The composition according to the invention may also comprise one or more standard additives that are well known in the art, other than the compounds defined previously. As examples of additives that may be used according to the invention, mention may be made of silanes, silicones, cationic polymers, anionic surfactants, amphoteric or zwitterionic surfactants, cationic surfactants, proteins, protein hydrolysates, vitamins, reducing agents, plasticizers, softeners, antifoams, moisturizers, plant, animal, mineral or synthetic oils, waxes, coloured or uncoloured mineral or organic pigments, dyes, clays, mineral fillers, UV screening agents, abrasive agents (pumice, apricot kernel powder), mineral colloids, peptizers, solubilizers, fragrances, preserving agents, pearlescent agents, propellants, antidandruff agents (for example, zinc pyrithione, octopirox®, selenium sulfide, ellagic acid and derivatives), hair-loss counteractants, hair restorers; anti-seborrhoeic active agents, and mixtures thereof.

The amounts of the various constituents in the compositions according to the invention are those conventionally used in the fields under consideration. Needless to say, these adjuvants must be of a nature and used in an amount such that they do not perturb the hair cleansing according to the invention. The amount of these adjuvants may range, for example, from 0.001% to 30% by weight relative to the total weight of the composition.

The viscosity of the composition according to the invention is generally between 100 and 5000 mPa.s, in particular between 300 and 3000 mPa.s and more particularly between 1000 and 2500 mPa.s, or even between 1100 and 2000 mPa.s.

The viscosity is measured at a shear rate of 1 s$^{-1}$ and at 25° C., for example with a Thermo Haake RS600 rotary rheometer with cone-plate geometry.

The pH of the compositions according to the invention is generally between 3 and 10, preferably from 3.5 to 8 and more particularly from 6 to 7.5. This pH may be adjusted by means of acidifying and basifying agents conventionally used in cosmetics.

The composition according to the invention generally comprises water and/or one or more organic solvents other than C2-C4 monoalcohols. Preferably, the composition also comprises water or a mixture of water and of organic solvent(s).

Organic solvents that may be mentioned include polyols, for instance propylene glycol, hexylene glycol and glycerol; polyol ethers such as dipropylene glycol, polyethylene glycols; C5-C10 alkanes; and mixtures thereof.

When the composition according to the invention comprises one or more organic solvents other than C2-C4 monoalcohols, these solvents may be present in a proportion of from 0.1% to 30% by weight and preferably 0.1% to 10% by weight relative to the total weight of the composition.

The compositions according to the invention preferably comprise from 20% to 79.9% by weight, more particularly from 30% to 75% by weight, even more preferentially from 40% to 70% by weight and preferentially from 50% to 65% by weight of water relative to the total weight of the composition.

The compositions according to the invention are prepared according to techniques that are well known to those skilled in the art.

The composition may be applied by hand, with an applicator nozzle, with a container equipped with a pump and a dispensing comb, or with an insoluble substrate impregnated with the composition.

The examples that follow will allow the invention to be understood more clearly, without, however, being limiting in nature. The amounts indicated are given as weight percentages of active materials, unless otherwise mentioned.

In the examples that follow, which are given as non-limiting illustrations, concrete compositions in accordance with the invention are given (AM means active material).

EXAMPLE 1

The following composition was prepared:

| | |
|---|---|
| Ethanol | 35 |
| Alkyl (C8/C16) polyglucoside (1.4) as an aqueous solution containing 53% active material (Plantacare 818 UP from Cognis) | 0.13 AM |
| Sodium hydroxide | 0.053 |
| Undecane/tridecane mixture | 5 |
| Acrylates/C10-30 alkyl acrylate crosspolymer (Carbopol Ultrez 21 Polymer from Noveon) | 0.28 AM |
| Fragrance | 0.3 |
| Triblock copolymer of ethylene oxide/propylene oxide/ethylene oxide (13 EO/30 PO/13 EO) (Synperonic PE/L 64 from Croda) | 1 |
| L-Menthol | 0.05 |
| pH agent qs | pH 6.7-7.3 |
| Water qs | 100% |

The composition is applied to dry hair, with the hands or directly from the conditioning. The scalp and the hair are massaged as for standard shampooing. The hair is combed and then wiped with a towel in order to remove the soiling. Drying is then performed, if necessary.

The composition was tested on 10 men and 10 women.

During application to dirty hair, the formulation was appreciated for its freshness, its ease of application and its ease of spreading, and also for its texture. After drying, the hair is clean, shiny, light, disentangled and easy to shape. The head of hair has a good volume, and does not show any residue. Furthermore, the composition provides a light styling effect.

The invention claimed is:

1. A composition comprising:
   (i) at least 20% by weight, relative to the total weight of the composition, of at least one $C_2$-$C_4$ monoalcohol,
   (ii) at least one polycondensate of ethylene oxide and of propylene oxide, and
   (iii) at least one nonionic surfactant other than the polycondensate (ii) chosen from $C_8$-$C_{30}$-alkyl polyglucosides.

2. The composition of claim 1 wherein the at least one nonionic surfactant is present in a concentration ranging from about 0.01% to about 5% by weight, relative to the total weight of the composition.

3. A composition according to claim 1, wherein the at least one $C_2$-$C_4$ monoalcohol is chosen from ethanol, isopropanol, tert-butanol and n-butanol, and mixtures thereof.

4. A composition according to claim 1, wherein the at least one $C_2$-$C_4$ monoalcohol is present in a concentration ranging from about 20% to about 70% by weight, relative to the total weight of the composition.

5. A composition according to claim 4, wherein the at least one $C_2$-$C_4$ monoalcohol is present in a concentration ranging from about 25% to about 45% by weight relative to the total weight of the composition.

6. A composition according to claim 1, wherein the at least one nonionic surfactant is present in a concentration ranging from about 0.1% to about 0.25% by weight, relative to the total weight of the composition.

7. A composition according to claim 1, wherein the at least one polycondensate (ii) is chosen from compounds of formula (I) below:

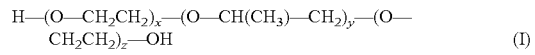

$$H-(O-CH_2CH_2)_x-(O-CH(CH_3)-CH_2)_y-(O-CH_2CH_2)_z-OH \qquad (I)$$

wherein x and z range from 2 to 150 and y ranges from 1 to 100.

8. A composition according to claim 7, wherein x and z range from 5 to 100 and y ranges from 10 to 80.

9. A composition according to claim 8, wherein x and z range from 10 to 20 and y ranges from 25 to 40.

10. A composition according to claim 7, wherein x and z are identical.

11. A composition according to claim 1, wherein the at least one polycondensate (ii) is present in a concentration ranging from about 0.1% to about 10% by weight, relative to the weight of the composition.

12. A composition according to claim 11, wherein the at least one polycondensate (ii) is present in a concentration ranging from about 0.5% to 5% by weight, relative to the total weight of the composition.

13. A composition according to claim 1, further comprising at least one additive chosen from silanes, silicones, cationic polymers, anionic surfactants, amphoteric or zwitterionic surfactants, cationic surfactants, proteins, protein hydrolysates, vitamins, reducing agents, plasticizers, softeners, antifoams, moisturizers, plant, animal, mineral or synthetic oils, waxes, colored or uncolored mineral or organic pigments, dyes, clays, mineral fillers, UV screening agents, abrasive agents, mineral colloids, peptizers, solubilizers, fragrances, preserving agents, pearlescent agents, propellants, antidandruff agents, hair-loss counteractants, hair restorers; and antiseborrhoeic active agents.

14. A composition according to claim 1, wherein the at least one nonionic surfactant is chosen from $C_8$-$C_{16}$ alkyl polyglucosides.

15. A process for cleansing the hair and/or the scalp, comprising applying to the hair and/or scalp a cosmetic composition comprising:
   (i) at least 20% by weight, relative to the total weight of the cosmetic composition, of at least one $C_2$-$C_4$ monoalcohol,
   (ii) at least one polycondensate of ethylene oxide and of propylene oxide, and
   (iii) at least one nonionic surfactant other than the polycondensate (ii) chosen from $C_8$-$C_{30}$-alkyl polyglucosides.

16. A process according to claim 15, wherein the cosmetic composition is applied to dry hair.

* * * * *